United States Patent
Tolmie et al.

(10) Patent No.: US 9,092,834 B2
(45) Date of Patent: Jul. 28, 2015

(54) SYSTEM AND METHOD FOR AUTOMATICALLY ADJUSTING MEDICAL DISPLAYS

(75) Inventors: Craig R. Tolmie, Stoughton, WI (US); Russell C. Ward, Stoughton, WI (US); Susan A. Meyers, Stoughton, WI (US); Robert J. Koch, Stoughton, WI (US)

(73) Assignee: General Electric Company, Schenectady, NY (US)

( * ) Notice: Subject to any disclaimer, the term of this patent is extended or adjusted under 35 U.S.C. 154(b) by 2525 days.

(21) Appl. No.: 11/298,769

(22) Filed: Dec. 9, 2005

(65) Prior Publication Data

US 2007/0180129 A1 Aug. 2, 2007

(51) Int. Cl.
*A61B 5/00* (2006.01)
*G06Q 50/22* (2012.01)

(52) U.S. Cl.
CPC ...................................... *G06Q 50/22* (2013.01)

(58) Field of Classification Search
None
See application file for complete search history.

(56) References Cited

U.S. PATENT DOCUMENTS

| | | | | |
|---|---|---|---|---|
| 4,051,522 A | * | 9/1977 | Healy et al. | 725/78 |
| 4,905,315 A | * | 2/1990 | Solari et al. | 318/640 |
| 5,526,146 A | * | 6/1996 | Goodman et al. | 349/5 |
| 5,867,821 A | | 2/1999 | Ballantyne et al. | |
| 5,991,730 A | * | 11/1999 | Lubin et al. | 705/3 |
| 6,322,502 B1 | * | 11/2001 | Schoenberg et al. | 600/300 |
| 6,419,630 B1 | | 7/2002 | Taylor, Jr. et al. | |
| 6,584,461 B1 | * | 6/2003 | Patel et al. | 707/3 |
| 6,600,421 B2 | | 7/2003 | Freeman | |
| 6,671,563 B1 | * | 12/2003 | Engelson et al. | 700/2 |
| 6,731,311 B2 | * | 5/2004 | Bufe et al. | 715/781 |
| 7,034,691 B1 | * | 4/2006 | Rapaport et al. | 340/573.1 |
| 7,134,130 B1 | * | 11/2006 | Thomas | 725/25 |
| 7,154,397 B2 | | 12/2006 | Zerhusen et al. | |
| 2001/0014769 A1 | | 8/2001 | Bufe et al. | |

(Continued)

FOREIGN PATENT DOCUMENTS

WO 2004088463 10/2004

OTHER PUBLICATIONS

Patientline: Clinicial Access Workflow Documentation website: http://patientline.prosite.co.uk/us/en/workflow_documentation.aspx, Date accessed: Sep. 19, 2006.

(Continued)

*Primary Examiner* — Lynsey Crandall
(74) *Attorney, Agent, or Firm* — Andrus Intellectual Property Law, LLP (57) ABSTRACT

A system and method for automatically adjusting medical displays is arranged to communicate medical information to a caregiver. The system includes at least one display for displaying medical information, a wireless communication device associated with the display and a wireless communication device associated with the caregiver. The wireless communication device associated with the display is arranged to realize if the wireless communication device associated with the caregiver, and thus the caregiver, is present in a predetermined area near the display. A controller associated with the display is arranged to automatically adjust at least one characteristic of the display based upon the realized presence of the caregiver. According to the method, the presence of the caregiver is detected when the caregiver enters the predetermined area near the display. At lease one characteristic of the display is thus adjusted automatically based upon the detected presence of the caregiver in the predetermined area.

16 Claims, 4 Drawing Sheets

(56) References Cited

U.S. PATENT DOCUMENTS

| | | | |
|---|---|---|---|
| 2001/0031071 A1 | 10/2001 | Nichols et al. | |
| 2001/0044588 A1 | 11/2001 | Mault | |
| 2002/0044059 A1* | 4/2002 | Reeder et al. | 340/573.1 |
| 2002/0115914 A1 | 8/2002 | Russ | |
| 2002/0149613 A1* | 10/2002 | Gutta et al. | 345/728 |
| 2003/0052787 A1* | 3/2003 | Zerhusen et al. | 340/573.1 |
| 2003/0103644 A1* | 6/2003 | Klayh | 382/100 |
| 2004/0078219 A1* | 4/2004 | Kaylor et al. | 705/2 |
| 2004/0148197 A1* | 7/2004 | Kerr et al. | 705/2 |
| 2004/0186357 A1 | 9/2004 | Soderbert et al. | |
| 2005/0086079 A1 | 4/2005 | Graves et al. | |
| 2005/0195330 A1* | 9/2005 | Zacks et al. | 348/564 |
| 2006/0286960 A1 | 12/2006 | Goehler | |
| 2006/0288095 A1* | 12/2006 | Torok et al. | 709/223 |
| 2007/0271115 A1* | 11/2007 | Baldus et al. | 705/2 |

OTHER PUBLICATIONS

Patientline: Patient Services—Patient Requests website: http://patientline.prosite.co.uk/us/en/patient_requests.aspx, Date accessed: Sep. 19, 2006.

Patientline: Patient Services—Education, website: http://patientline.prosite.co.uk/us/en/education.aspx, Date accessed: Sep. 19, 2006.

Patientline: Patient Services—Food Ordering, website: http://patientline.prosite.co.uk/us/en/food_ordering.aspx, Date accessed: Sep. 19, 2006.

Patientline: Patient Services—Satisfaction Surveys, website: http://patientline.prosite.co.uk/us/en/satisfaction_survey.aspx, Date accessed: Sep. 19, 2006.

Patientline: Clinical Access, website: http://patientline.prosite.co.uk/us/en/clinical_access.aspx, Date accessed: Sep. 19, 2006.

Patientline: Patient Services, website: http://patientline.prosite.co.uk/us/en/patient_services_.aspx, Date accessed: Sep. 19, 2006.

Patientline: Patient Entertainment & Communications—External Communication, website: http://patientline.prosite.co.uk/us/en/external_communication.aspx, Date accessed: Sep. 19, 2006.

Patientline: Patient Entertainment & Communications—Entertainment Center, website: http://patientline.prosite.co.uk/us/en/entertainment_center.aspx, Date accessed: Sep. 19, 2006.

Patientline: Clinical Access—Medication Administration, website: http://patientline.prosite.co.uk/us/en/medication_administration.aspx, Date accessed: Sep. 19, 2006.

Patientline: Product Overview & Testimonials—Product Benefits, website: http://patientline.prosite.co.uk/us/en/product_benefits.aspx, Date accessed: Sep. 15, 2006.

Cardinal Health—Our Products p Pyxis Patient Station, website: http://www.pyxis.com/prodDetails.aspx?pid=55, Date accessed: May 14, 2007.

GB Search Report dated Jun. 10, 2008.

* cited by examiner

SYSTEM AND METHOD FOR AUTOMATICALLY ADJUSTING MEDICAL DISPLAYS

BACKGROUND AND SUMMARY

The present invention relates to the healthcare environment and the ongoing need for improved efficiency in the healthcare workplace and improved safety for patients. In the healthcare workplace, increasing amounts of patient/medical information is communicated by visual display units, such as, for example, physiological monitors, life support system displays, hospital information system computer displays, and the like. Such visual display units typically include a computer screen or monitor that remains stationary relative to the caregivers moving about the workplace. Because of the critical nature of most patient/medical information it is often paramount for caregivers to maintain visual contact with the visual display units for continuous periods while pursuing other physical and intellectual tasks in the workplace. For example, patient vital signs are normally referred to at regular intervals to ensure that proper care is being provided to the patient. It is a problem however that the movement of caregivers in the workplace often places the caregivers in positions that are beyond acceptable viewing range of the display units. In many cases, visibility is reduced to zero as the caregivers move to either side of the display device or otherwise outside of the viewing range for the device.

In cases where the patient is being transported from one location to another, critical data, such as patient vital signs, are displayed by monitoring devices that are placed somewhere on or around the bed. Such an arrangement requires the caregiver to walk to a specific position, often backwards, to be able to see the display while managing the mobility of the bed. In addition, glare from ambient light sources can also reduce the viewability of the display screen if the caregiver is viewing the screen from a particular angle. The caregiver must therefore change his/her position or manually adjust the viewing angle of the display. Known arrangements are thus inefficient in that they require the caregiver to spend time and effort to view the display. This time and effort could alternatively be spent providing better care to the patient.

In addition, various caregivers have different data interests and prefer patient/medical information to be displayed in a configuration that suits these interests. For example, a particular data layout that is preferred by a cardiologist can be significantly different than that of a respiratory therapist. Known arrangements require caregivers having different data interests to manually change the type of information shown on the visual display. This takes time, which could be spent providing better care to the patient.

SUMMARY OF THE INVENTION

The present invention provides an improved and more efficient system and method for communicating medical information to a caregiver. According to the system and method of the present invention, critical and non-critical patient/medical information is communicated by visual display units in an efficient manner and such that the caregiver is able to freely move about the workplace and/or patient care area while maintaining visual contact with one or more of the visual display units.

In one arrangement, the system for communicating medical information to a caregiver includes a display for displaying the medical information, a first wireless communication device associated with the display, and a second wireless communication device associated with the caregiver. The first communication device is arranged to realize if the second communication device, and thus the caregiver, is located in a predetermined area near the display. A controller associated with the display is arranged to automatically adjust at least one characteristic of the display based upon the realized presence of the caregiver.

In a further arrangement, the controller is arranged to control the orientation of the display based upon the position of the caregiver to provide enhanced viewing of the display by the caregiver. The position of the caregiver may, for example, be obtained by triangulating the position of the caregiver. In another arrangement, the controller may change the quality and/or quantity of medical information on the display. This arrangement is particularly useful when different caregivers have different specialized patient data and/or medical information interests.

In one example of the method of the invention, the display of medical information on a display is automatically adjusted based upon the detected presence of the caregiver when the caregiver enters a predetermined area near the display. At least one characteristic of the display is automatically adjusted, such as the physical orientation of the display and/or a characteristic of the patient/medical information provided on the display. The method may also include the step of prioritizing a plurality of caregivers present in the predetermined area. In this example, the characteristic of the display is adjusted based upon a predetermined setting assigned to the caregiver within the area that has the highest priority.

Various other objects and advantages of the present invention will be recognized with reference to the following detailed description and drawings.

BRIEF DESCRIPTION OF THE DRAWINGS

Preferred embodiments of and the best mode for carrying out the present invention are described hereinbelow with reference to the attached drawing figures, wherein.

DETAILED DESCRIPTION OF THE PREFERRED EMBODIMENTS

In the preferred embodiments of the present invention described in detail below, a system and method for communicating medical information to a caregiver is provided. It should be understood that the drawings and specification are to be considered an exemplification of the principles of the invention, which is more particularly defined in the appended claims.

The present invention relates to a system and method whereby at least one characteristic of a display for displaying medical information is automatically adjusted based upon the presence and/or location of a caregiver within a predetermined area near the display. The at least one characteristic may include for example the physical orientation of the display unit, the type of patient/medical information on the display, or the layout of patient/medical information on the display.

Figure 1:
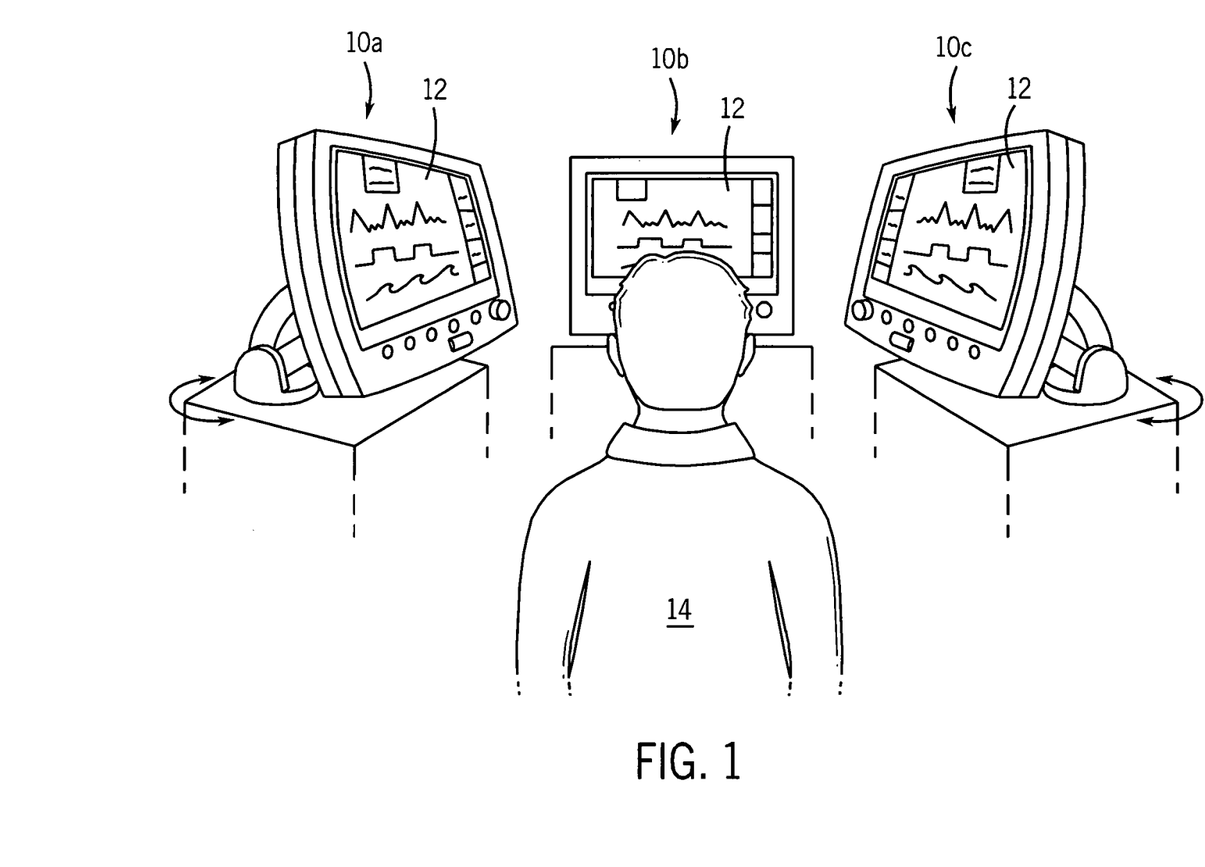
FIG. 1 is a perspective view of a plurality of visual display units being viewed by a caregiver.

Referring to FIG. 1, a representation of a medical workplace, such as a hospital room, is shown. In a typical hospital room, one or more medical display units 10a, 10b, 10c communicate patient and/or other medical information to caregivers, patients and other occupants in the room. Patient information may include vital signs for the patient, or medical apparatus settings, such as for example, ventilator settings or anesthesia machine settings. The information may also include alarm information for monitoring and/or patient care apparatus that is being used to treat the patient. Medical information may include for example general hospital information, alarm information, and/or hospital employee location information. Much of the information that is displayed on medical display units can be critical and often needs to be closely monitored by the caregivers working in the medical workplace.

In known arrangements, the visual display units 10a, 10b, 10c comprise computer monitors having flat display screens 12 that are static in orientation and convey a particular type of information in a particular layout and in a limited line of sight. The medical display units 10a, 10b, 10c can be located integrally with medical apparatus such as the aforementioned ventilators or anesthesia machines. Alternatively, or in addition, the medical display units may be coupled with mobile medical equipment or hospital room furniture, such as patient beds. Of course, the display units can also be stand-alone units.

As the caregiver 14 moves about the workplace, the caregiver 14 often moves outside the line of sight of the display screens 12. At such times, the caregiver 14 is unable to view the patient/medical information, which often can be critical information that needs to be monitored on a regular basis, especially during clinical care procedures. At other times, a caregiver 14 enters the medical workplace and has particular interests and desires to quickly review a particular type and/or layout of patient/medical information that is different from the information currently available on the display. As discussed above, current systems and methods unfortunately require the caregiver 14 to manually control the display to obtain the desired display and/or layout of information.

Figure 2:
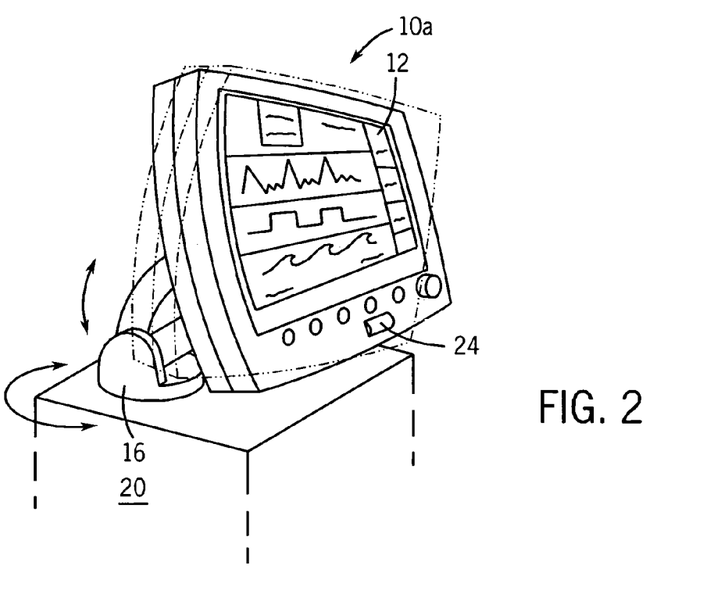
FIG. 2 is a perspective view of a rotatably mounted visual display unit.

Referring to FIG. 2, according to one example of the present invention, at least one visual display unit 10a that displays patient/medical information is robotically positionable into different orientations based upon the location of a caregiver 14 in a predetermined area near the display thus maintaining optimum caregiver viewing.

In the particular example shown in FIG. 2, the medical display unit 10a is mounted on a swivel stand 16 that is free to automatically rotate 360° about a vertical axis. The display screen 12 can also be automatically tilted 180° about a horizontal axis along a hinge connection (not shown). The automatic movements of the medical display unit 10a are driven by a motor drive mechanism (shown schematically as 20) that is controlled by a controller (shown schematically in FIG. 6 as 22 and further discussed below). The mounting hardware for the display 10a may include means to prevent rotation beyond 360° to reduce display and power cable fouling. In the event of mechanical or power failure the display 10a can be repositioned manually.

A first wireless communication device is provided on the medical display unit 10a. In the embodiment shown, the first wireless communication device includes a transceiver 24 that is arranged to send and/or receive signals within a predetermined area about the medical display unit 10a.

Figure 3:
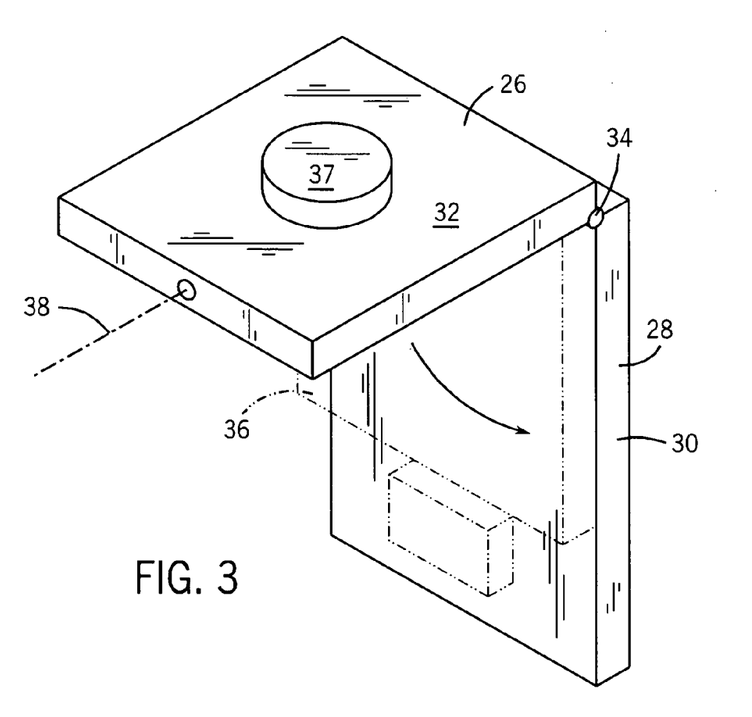
FIG. 3 is a perspective view of a portable communication device.

Referring to FIG. 3, a transponder 26 is arranged to be carried by the caregiver 14 and communicate with the transceiver 24 on the display unit 10a. The transponder 26 is arranged to send and/or receive signals from the transceiver 24 on the display unit 10a. In a preferred embodiment, the transponder 26 comprises part of an identification badge 28 for the caregiver 14 and has a base unit 30 and an active unit 32, which are connected by a movable hinge 34. The hinge 34 allows the active unit 32 to fold down into resting position 36 (shown in dotted lines).

Communication between the first communication device or transceiver 24 and the second communication device or transponder 26 is preferably wireless and may comprise radio-frequency signals, infra-red signals, and/or the like. For example, a remote control signal may be actively emitted from a radio frequency transmitter on the transceiver 24 over, for example, a 50 feet radius to establish contact with any transponder 26 in the zone. Alternatively, the transceiver 24 may be passive and the transponder 26 arranged to emit a remote control signal 38 to actively locate the transceiver 24. In use, the transponder 26 may be fastened to the clothing of the caregiver 14 by an appropriate clip on the back of base unit 30. A manual override button 37 is provided on the transponder 26 to prevent further system adjustment or re-configurations, thus allowing for the higher level of user interaction.

Figure 4A:
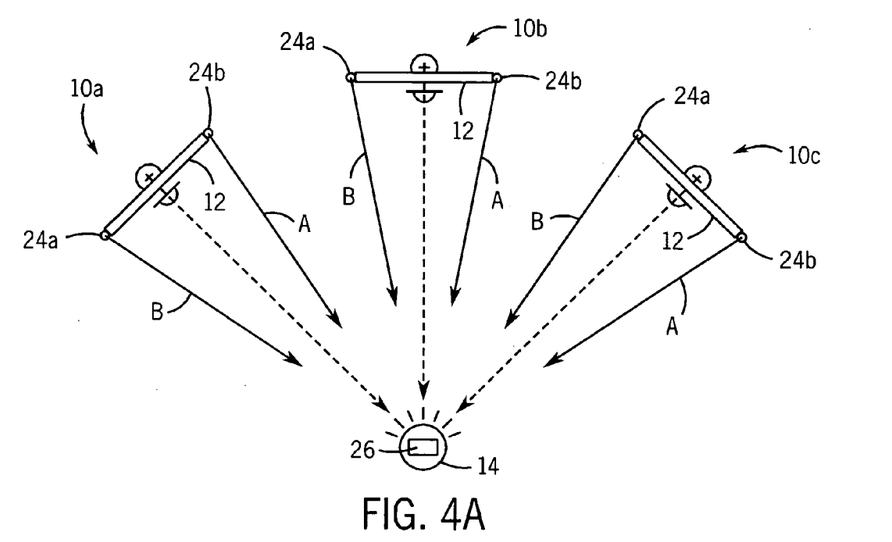
FIG. 4a is a schematic top view of the plurality of displays directed towards a caregiver.
Figure 4B:
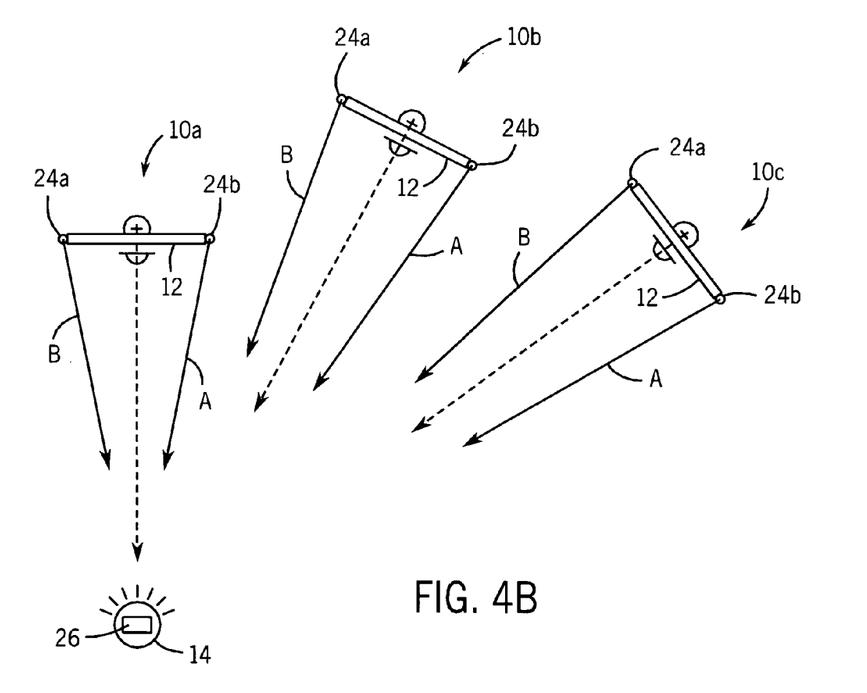
FIG. 4b is a schematic top view of the plurality of displays following the caregiver as the caregiver moves about a workplace.
Figure 6:
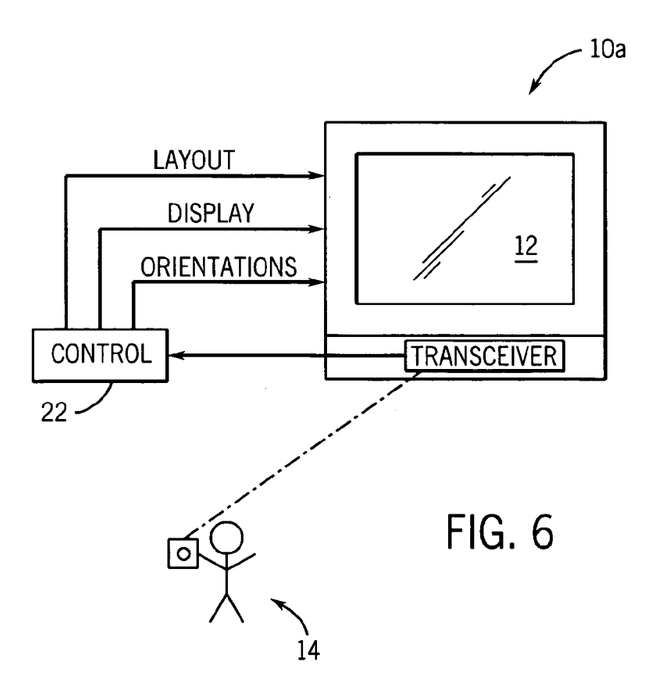
FIG. 6 is an illustrative view of one embodiment of the system of the present invention.

Referring to FIG. 6, controller 22 is arranged to control the at least one characteristic of the medical display 10a, 10b, 10c. For example, the controller 22 can be arranged to control the physical orientation of the medical display unit 10a, 10b, 10c as it relates to the caregiver 14 by controlling motor 20. This type of arrangement is shown in FIGS. 4A, 4B, and 6. In this example, the display units 10a, 10b, 10c include means for triangulating the location of the caregiver within the predetermined area monitored by the first communication device 24. More specifically, the display units comprise a pair of transceivers 24a, 24b on either side of the display screen 12. The pair of transceivers 24 communicate with the transponder 26 carried by the caregiver and are adapted to determine the distance A and B between the transponder 26 and transceiver 24. Based upon the distances, the location of the caregiver can be determined by the controller 22 using basic triangulation time of flight theory that is well known in the art.

Each of the visual display units 10a, 10b, 10c are shown in FIG. 4A oriented such that the caregiver is located at a 90° angle from the flat display screen 12. As shown in FIG. 4B, as the caregiver enters or moves in the workplace, the controller 22 adjusts the orientation of the medical display units 10a, 10b, 10c continuously or periodically such that each flat display screen 12 remain at a 90° angle from the caregiver 14. Therefore, the display screens 12 are constantly viewable by the caregiver 14. It will be recognized that when the caregiver initially enters a predetermined area near the visual display units 10a, 10b, 10c, the screens of the display units will typically not be oriented at 90° from the caregiver. As such, when the caregiver enters the predetermined area, the transceiver 24 and transponder 26 communicate to locate the position of the transponder 26. Based upon this calculated position, the controller 22 robotically adjusts the physical orientation of the display units 10a, 10b, and 10c to orient the screens at 90° from the caregiver. Of course the controller 22 can also adjust the vertical tilt of the screens 12 to align the screens 12 with the caregiver 14 based on the triangulation principles discussed above.

Referring to FIG. 6, the controller 22 may further or alternately be arranged to automatically adjust the display of patient/medical information or content on the screen 12 based upon the existence of a particular transponder 26 within the predetermined area of the transceiver 24. For example, each transponder 26 may be programmable with a particular data choice of the particular caregivers specialty of care 14. Therefore, when the caregiver 14 enters the predetermined area, the controller 22 adjusts the display to match the particular data set assigned to the transponder 26. Similarly, the layout of information on the display screen 12 can be adjusted based upon a predetermined layout programmed into the transponder 26. In one example, the transponder 26 is programmed to include up to five personal display layout configuration preferences of the caregiver. Programming of the transponder is achieved by using PC computer software from which the user selects or builds a configuration of each of the five configuration preferences. When the caregiver is within the predetermined area near the display, the transponder 26 and transceiver 24 communicate to provide the controller with the particular configuration programmed on the transponder 26. The controller then re-configures the display automatically. Each transponder may have a default configuration. In this example, through the use of the button 37 on the transponder, the user can sequentially scroll through all five display configurations according to their preference.

In one example, the transponder 26 is programmable with a priority assigned to the particular caregiver carrying the identification badge 28. This aspect allows the controller 22 to prioritize and select certain display characteristics based upon a plurality of caregivers present in the predetermined area. For example the controller 22 may be programmed to assign the highest priority to the highest ranking doctor present in the room, the next priority to the highest ranking nurse, etc. Therefore when a caregiver having a higher ranking enters the room, the display characteristics are automatically changed by the controller 22. If there are more than one display in the room, the controller 22 may assign each caregiver a particular display screen to display that caregiver's display preferences. In this example the manual override button 37 on the transponder 26 allows any of the users present to override the priority scheme and designate themselves as the primary view. The override can be eliminated by pressing the button 37 again or simply leaving the predetermined area. When the override is eliminated the controller 22 reverts to the programmed priority. When two or more users that have the same priority status are in the predetermined area, the controller 22 assumes that the first user to enter the predetermined area has priority.

Figure 5:
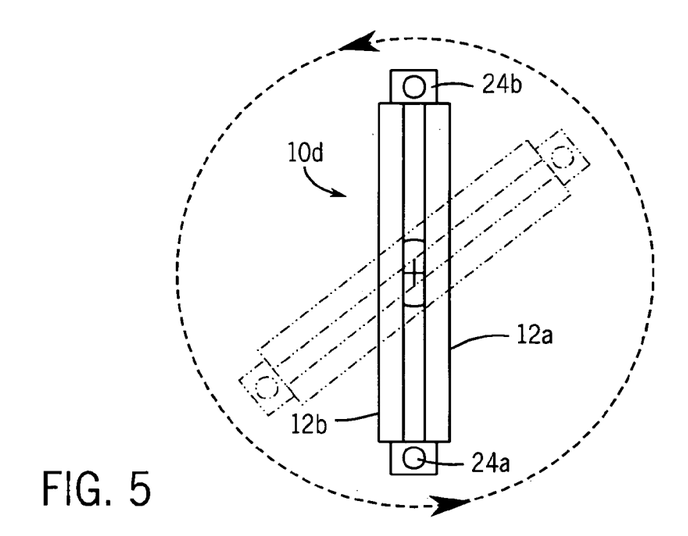
FIG. 5 is a top view of a double-sided visual display unit that is rotatable about a central axis.

Referring to FIG. 5, a further embodiment of the medical display unit 10d is shown. The medical display unit 10d includes opposing display screens 12a, 12b, which provide more versatile and enhanced 360° viewing area. Because the medical display unit 10d can typically comprise audio and video cords, it is often desirable, although not necessary, to limit the rotation of the display unit to 180° about its vertical axis. This will prevent the cords from becoming tangled.

While this invention is susceptible to embodiments in many different forms, the drawings and specification describe in detail a preferred embodiment of the invention. They are not intended to limit the broad aspects of the invention to the embodiment illustrated.

What is claimed is:

1. A system for communicating medical information to a caregiver, the system comprising:
a display that presents patient/medical information of a first information type;
a first wireless communication device associated with a first caregiver and transmitting a first signal indicative of patient/medical information of a predetermined second information type;
a second wireless communication device associated with the display, the second wireless communication device configured to receive the first signal from the first wireless communication device, when the first wireless communication device is within a predetermined distance of the display;
a third wireless communication device associated with a second caregiver and the third wireless communication device transmits a second signal indicative of patient/medical information of a third information type, the third wireless communication device further comprising a button, upon activation of the button, the third wireless device produces a third signal; and
a controller in communication with the second wireless communication device and the display, the controller automatically identifies the patient/medical information of the predetermined second information type from the first signal from the first wireless communication device and automatically adjusts the patient/medical information of the first information type displayed on the display to the patient/medical information of the predetermined second information type, the patient/medical information of the predetermined second information type specifically tailored to the specific caregiver;
wherein when the second wireless communication device received the first signal and the second signal, the controller selects between the patient/medical information of the predetermined second information type and the patient/medical information of the third information type based upon a programmed hierarchy of received wireless signals based upon the specific caregivers associated with each of the first and third wireless communication devices, and if the controller selects the patient/medical information of the predetermined second information type, and the controller further receives the third signal through the second wireless communication device, the controller overrides the programmed hierarchy and automatically adjusts the patient/medical information of the predetermined second information type to the patient/medical information of the predetermined third information type.

2. The system of claim 1 further comprising:
a fourth wireless communication device associated with the display and configured to receive the signal from the first wireless communication device;
wherein the controller further determines a location of the first caregiver with respect to the display from the first signal received by the second and fourth wireless communication devices.

3. The system of claim 2 wherein the controller automatically adjusts the display configuration of the patient/medical information of the predetermined second information type, specifically tailored to the first caregiver on the display, further based upon the determined location of the first caregiver.

4. The system of claim 1, wherein the signal transmitted by the first wireless communication device is an identifying signal that uniquely identifies the first caregiver, the second wireless communication device receives the identifying signal, and the controller automatically adjusts the patient/medical information of the first information type on the display according to a stored patient/medical information of the predetermined second information type specific to the uniquely identified first caregiver.

5. The system of claim 4, wherein instructions for the controller to automatically adjust the patient/medical information of the first information type on the display are programmed on the first communication device and communicated by the first communication device to the controller through the second communication device.

6. The system of claim 4, further comprising a plurality of displays, wherein the controller is arranged to automatically adjust the patient/medical information of the predetermined second information type, specifically tailored to the first caregiver, of the plurality of displays based upon the realized presence of the first caregiver.

7. The system of claim 4, wherein the layout of the patient/medical information of the first information type is automatically adjusted to a stored predetermined layout of the patient/medical information of the second information type specific to the first caregiver.

8. The system of claim 7, wherein the stored predetermined layout of information is personalized based recorded the preferences of the uniquely identified first caregiver.

9. The system of claim 1, wherein the display is a first display and further comprising a second display, and the controller automatically presents the patient/medical information of the second information type on the second display.

10. The system of claim 1, wherein the patient/medical information of the first information type is different from the second information type and the first information type and second information type are selected from: patient vital signs information, alarm information, anesthesiology information, cardiology information, and respiratory therapy information.

11. A system for communicating medical information to a caregiver, the system comprising:
  a display that presents first patient/medical information;
  a first wireless communication device associated with a first caregiver and transmitting a first signal indicative of second patient/medical information, the first wireless communication device further comprising a button, upon activation of the button, the first wireless communication device produces a second signal;
  a second wireless communication device associated with the display, the second wireless communication device configured to receive signals from the first wireless communication device, when the first wireless communication device is within a predetermined distance of the display;
  a third wireless communication device associated with a second caregiver and the third wireless communication device transmits a third signal indicative of third patient/medical information, the third wireless communication device further comprising a button, upon activation of the button, the third wireless communication device produces a fourth signal; and
  a controller in communication with the second wireless communication device and the display, the controller identifies the second patient/medical information from the first signal from the first wireless communication device and automatically adjusts the first patient/medical information displayed on the display to the second patient/medical information, the second patient/medical information specifically tailored to the first caregiver;
  wherein when the second wireless communication device receives signals from both the first wireless communication device and the third wireless communication device, the controller selects between the second patient/medical information and the third patient/medical information based upon a programmed hierarchy of received wireless signals based upon the specific caregivers associated with each of the first and third wireless communication devices and
  if the controller selects the second patient/medical information based upon the programmed hierarchy, and the controller further receives the fourth signal through the second wireless device, the controller overrides the programmed hierarchy and automatically adjusts the second patient/medical information displayed on the display to the third patient/medical information.

12. The system of claim 11, wherein the second signal is selected from a plurality of signals, each signal of the plurality of signals indicative of a different display configuration of the patient/medical information presented on the display and wherein sequential activation of the button of the first wireless communication device selects the second signal from the plurality of signals and the controller automatically adjusts the patient/medical information displayed on the display to the configuration indicated by the second signal.

13. A system for communicating medical information to a caregiver, the system comprising:
  a display that presents first patient/medical information, the display being movable about at least one axis;
  a first wireless communication device associated with a first caregiver and transmitting a first signal indicative of second patient/medical information;
  a second wireless communication device associated with a second caregiver and transmitting a second signal indicative of a third patient/medical information, the second wireless communication device further comprising a button, upon activation of the button, the second wireless communication device produces a third signal;
  a third wireless communication device associated with the display, the second wireless communication device configured to receive the first signal from the first wireless communication device, when the first wireless communication device is within a predetermined distance of the display and the second signal from the second wireless communication device, when the second wireless communication is with a predetermined distance of the display; and
  a controller in communication with the third wireless communication device and the display, the controller receives the first signal and the second signal and selects between the second patient/medical information and the third patient/medical information based upon a programmed hierarchy of received wireless signals based upon the specific caregivers associated with each of the first and second wireless communication devices and automatically adjusts the first patient/medical information displayed on the display to the selected second or third patient/medical information, wherein the controller identifies a position of the first or second wireless communication device associated with the selected second or third patient/medical information and operates the display to move the display about the at least one axis to automatically adjust a physical orientation of the display relative to the position of the first or second wireless device associated with the selected second or third patient/medical information;
  wherein if the controller selects the second patient/medical information and the controller receives the third signal, the controller overrides the programmed hierarchy and automatically adjusts the second patient/medical information to the third patient/medical information.

14. The system of claim 13, further comprising a motor secured to the display, the motor being operable by the controller to automatically adjust the physical orientation of the display.

15. The system of claim 14, wherein the physical orientation of the display is automatically adjusted to be orthogonal to the first or second wireless device associated with the selected second or third patient/medical information.

16. The system of claim 15, further comprising:
a fourth wireless communication device associated with the display, the third wireless communication device configured to receive the first signal from the first wireless communication device, when the first wireless communication device is within the predetermined distance of the display and configured to receive the second signal from the second wireless communication device, when the second wireless communication device is within the predetermined distance of the display;
wherein the controller identifies the position of the first wireless communication device by translation of the first signal received at the third wireless communication device and the fourth wireless communication device and identifies the position of the second wireless communication device by triangulation of the second signal received at the third wireless communication device and the fourth wireless communication device.

\* \* \* \* \*